US00PP22868P2

(12) United States Plant Patent
Misato

(10) Patent No.: US PP22,868 P2
(45) Date of Patent: Jul. 24, 2012

(54) ***MANDEVILLA* PLANT NAMED 'SUNPARAMIHO'**

(50) Latin Name: *Mandevilla×amabilis*
Varietal Denomination: Sunparamiho

(75) Inventor: Tomoya Misato, Yamanashi (JP)

(73) Assignee: Suntory Flowers Ltd., Tokyo (JP)

( * ) Notice: Subject to any disclaimer, the term of this patent is extended or adjusted under 35 U.S.C. 154(b) by 147 days.

(21) Appl. No.: 12/804,921

(22) Filed: Jul. 30, 2010

(51) Int. Cl.
*A01H 5/00* (2006.01)

(52) U.S. Cl. ..... Plt./232

(58) Field of Classification Search ..... Plt./232
See application file for complete search history.

*Primary Examiner* — Annette Para
(74) *Attorney, Agent, or Firm* — C. A. Whealy

(57) ABSTRACT

A new and distinct cultivar of *Mandevilla* plant named 'Sunparamiho', characterized by its vining plant habit; vigorous growth habit; glossy leaves; freely branching habit; freely flowering habit; and medium-sized white-colored flowers; and long flowering period.

1 Drawing Sheet

Botanical designation: *Mandevilla×amabilis*.
Cultivar denomination: 'SUNPARAMIHO'.

BACKGROUND OF THE INVENTION

The present invention relates to a new and distinct cultivar of *Mandevilla* plant, botanically known as *Mandevilla×amabilis* and hereinafter referred to by the name 'Sunparamiho'.

The new *Mandevilla* plant is a product of a planned breeding program conducted by the Inventor in Higashiomi, Shiga, Japan. The objective of the breeding program is to create new vining and freely-branching *Mandevilla* plants with numerous white-colored flowers.

The new *Mandevilla* plant originated from a cross-pollination made by the Inventor in Higashiomi, Shiga, Japan in April, 2004, of a proprietary selection of *Mandevilla×amabilis* identified as code number M7, not patented, as the female, or seed parent with a proprietary selection of *Mandevilla×amabilis* identified as code number M1, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2005.

Asexual reproduction of the new *Mandevilla* plant by cuttings in Higashiomi, Shiga, Japan, since November, 2005, has shown that the unique features of this new *Mandevilla* plant are stable and reproduced true to type in successive generations.

SUMMARY OF THE INVENTION

Plants of the new *Mandevilla* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunparamiho'. These characteristics in combination distinguish 'Sunparamiho' as a new and distinct *Mandevilla* plant:

1. Vining plant habit.
2. Vigorous growth habit.
3. Glossy leaves.
4. Freely branching and flowering habit.
5. Medium-sized white-colored flowers.
6. Long flowering period.

Plants of the new *Mandevilla* can be compared to plants of the female parent selection. Plants of the new *Mandevilla* differ primarily from plants of the female parent selection in the following characteristics:

1. Plants of the new *Mandevilla* have shorter internodes than plants of the female parent selection.
2. Plants of the new *Mandevilla* have smaller leaves than plants of the female parent selection.
3. Plants of the new *Mandevilla* have smaller flowers than plants of the female parent selection.

Plants of the new *Mandevilla* can be compared to plants of the male parent selection. Plants of the new *Mandevilla* differ primarily from plants of the male parent selection in the following characteristics:

1. Plants of the new *Mandevilla* have longer internodes than plants of the male parent selection.
2. Plants of the new *Mandevilla* have larger leaves than plants of the male parent selection.
3. Plants of the new *Mandevilla* have larger flowers than plants of the male parent selection.

Plants of the new *Mandevilla* can be compared to plants of the *Mandevilla* 'Sunmandeho', disclosed in a U.S. Plant Pat. No. 11,556. In side-by-side comparisons conducted in Higashiomi, Shiga, Japan, plants of the new *Mandevilla* differed from plants of 'Sunmandeho' in the following characteristics:

1. Leaves of plants of the new *Mandevilla* were glabrous whereas leaves of plants of 'Sunmandeho' were pubescent.
2. Plants of the new *Mandevilla* had smaller flowers plants of 'Sunmandeho'.
3. Plants of the new *Mandevilla* were more freely flowering than plants of 'Sunmandeho'.
4. Plants of the new *Mandevilla* had smaller flowers than plants of 'Sunmandeho'.

5. Petal apices of plants of the new *Mandevilla* were rounded whereas petal apices of plants of 'Sunmandeho' were cuspidate.
6. Plants of the new *Mandevilla* had longer peduncles than plants of 'Sunmandeho'.

BRIEF DESCRIPTION OF THE PHOTOGRAPHS

The accompanying colored photographs illustrate the overall appearance of the new *Mandevilla* plant, showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparamiho' grown in a container.

The photograph at the bottom of the sheet is a close-up view of a typical flowering plant of 'Sunparamiho'.

DETAILED BOTANICAL DESCRIPTION

The aforementioned photographs and following observations, measurements and values describe plants grown in 15-cm containers in Higashiomi, Shiga, Japan, under commercial practice during the summer in an outdoor nursery. During the production of the plants, day temperatures averaged 25° C. and night temperatures averaged 15° C. Plants were five months old when the photographs and description were taken. In the following description, color references are made to The Royal Horticultural Society Colour Chart, 2001 Edition, except where general terms of ordinary dictionary significance are used.

Botanical classification: *Mandevilla×amabilis* 'Sunparamiho'.

Parentage:

*Female, or seed, parent*.—Proprietary selection of *Mandevilla×amabilis* identified as code number M7, not patented.

*Male, or pollen, parent*.—Proprietary selection of *Mandevilla×amabilis* identified as code number M1, not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; moderately dense.

Plant description:

*Plant and growth habit*.—Vining plant habit; vigorous growth habit; freely branching habit.

*Plant height*.—About 128 cm.

*Lateral branch description*.—Diameter: About 3.7 mm. Internode length: About 13.9 cm. Strength: Strong. Texture: Smooth, glabrous. Color, young: Close to 144A. Color, mature: Close to N199A to N199B.

Foliage description:

*Arrangement*.—Opposite, simple.

*Length*.—About 14 cm.

*Width*.—About 6 cm.

*Shape*.—Narrowly elliptic.

*Apex*.—Cuspidate.

*Base*.—Obtuse.

*Margin*.—Entire.

*Texture, upper and lower surfaces*.—Smooth, glabrous.

*Luster, upper and lower surfaces*.—Glossy.

*Venation pattern*.—Pinnate, reticulate.

*Color*.—Developing leaves, upper and lower surfaces: Close to 144A. Fully expanded leaves, upper surface: Close to 147A; venation, close to 145A. Fully expanded leaves, lower surface: Close to 137C; venation, close to 145D.

*Petiole length*.—About 1.5 cm.

*Petiole diameter*.—About 2.5 mm.

*Petiole texture, upper and lower surfaces*.—Smooth, glabrous.

*Petiole color, upper and lower surfaces*.—Close to 144A to 144C.

Flower description:

*Flower type and habit*.—Single salverform flowers; flowers arranged in axillary racemes; flowers face mostly outwardly; freely flowering habit with about seven to nine flowers per inflorescence.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—Faint, pleasant.

*Inflorescence height*.—About 17.6 cm.

*Inflorescence diameter*.—About 10.2 cm.

*Flowers*.—Appearance: Flared trumpet, corolla fused and five-parted; flowers roughly star-shaped. Diameter: About 7 cm. Depth (length): About 5.7 cm. Throat diameter: About 1.5 cm. Tube length: About 4.7 cm. Tube diameter, mid-section: About 1.1 cm. Tube diameter, base: About 3.5 mm.

*Flower buds*.—Height: About 6.5 cm. Diameter: About 1.4 cm. Shape: Lenticular. Color: Close to 145B and 157D.

*Corolla*.—Arrangement/appearance: Single whorl of five petals, fused at the base. Petal length: About 2.8 cm. Petal width: About 3.2 cm. Petal shape: Roughly spatulate. Petal apex: Rounded. Petal margin: Entire; slightly undulate. Petal texture, upper and lower surfaces: Smooth, glabrous. Throat texture: Smooth, glabrous. Tube texture: Smooth, glabrous. Color: Petal, when opening and fully opened, upper surface: Close to 155C. Petal, when opening and fully opened, lower surface: Close to 155C. Throat: Close to 15A; toward the base, close to 15B. Tube: Close to 155A, towards the apex, close to 145A.

*Corona*.—Arrangement/appearance: Single whorl of five sepals. Sepal length: About 5 mm. Sepal width: About 2.1 mm. Sepal shape: Lanceolate. Sepal apex: Acute. Sepal base: Truncate. Sepal margin: Entire. Sepal texture, upper and lower surfaces: Smooth, glabrous. Sepal color: Immature, upper and lower surfaces: Close to 145A. Mature, upper and lower surfaces: Close to 145A.

*Peduncles*.—Length: About 3.7 cm. Diameter: About 2.6 mm. Texture: Smooth, glabrous. Strength: Flexible, but strong. Color: Close to 143B.

*Pedicels*.—Length: About 2.6 cm. Diameter: About 2.6 mm. Texture: Smooth, glabrous. Strength: Flexible, but strong. Color: Close to 145B.

Reproductive organs.—Stamens: Quantity/arrangement: Typically five; filaments fused to corolla; anthers, connivent. Anther shape: Ellipsoidal. Anther size: About 8.6 mm by 1.3 mm. Anther color: Close to 18C. Pollen amount: Moderate. Pollen color: Close to 18C. Pistils: Quantity: Typically one. Pistil length: About 2.25 cm. Style color: Close to 145C. Stigma shape: Conical. Stigma color: Close to 144C. Ovary color: Close to 144C.

*Seed/fruit*.—Seed and fruit production have not been observed.

Disease/pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparamiho' as illustrated and described.

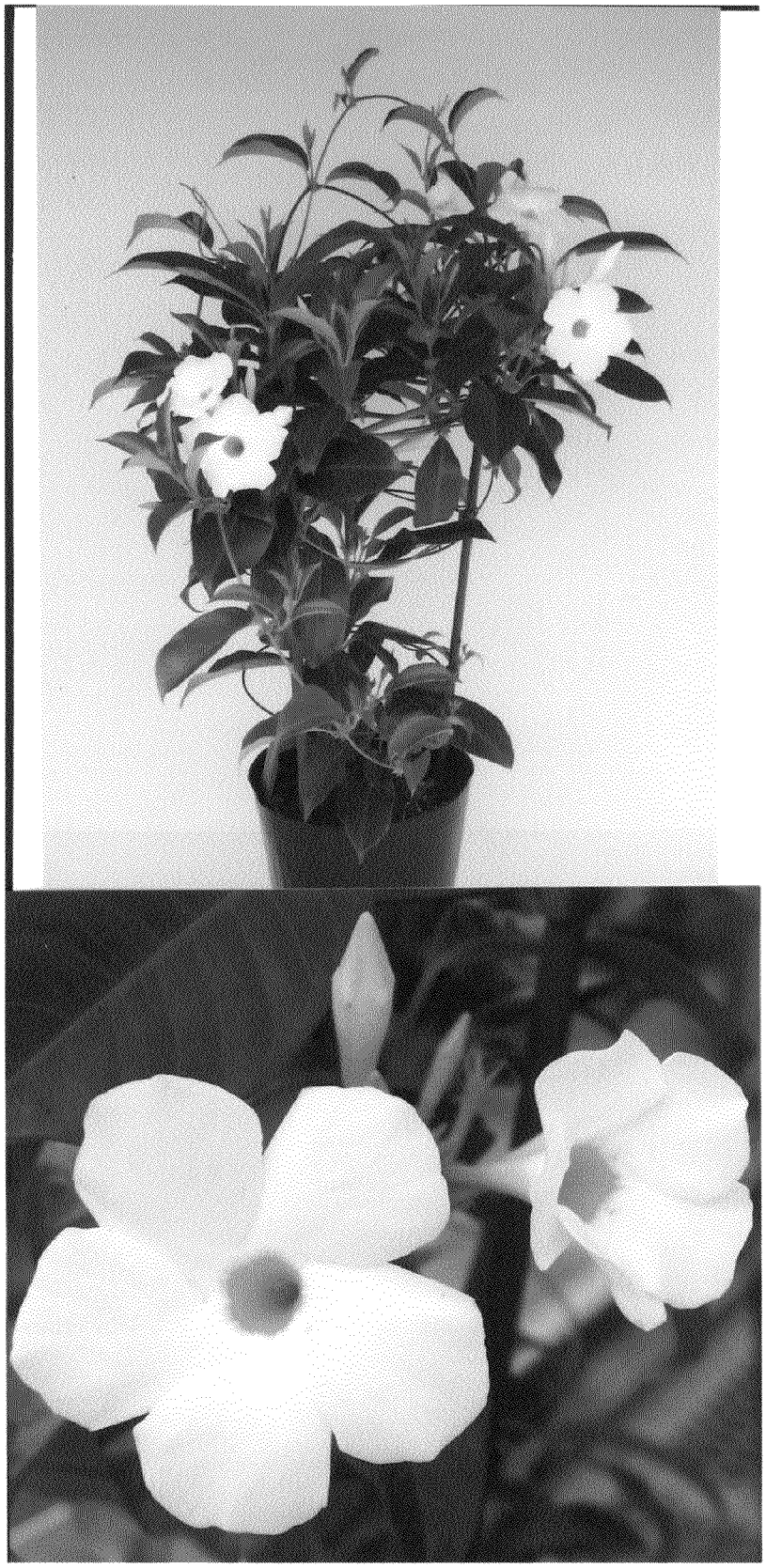

* * * * *